(12) United States Patent
Brummer et al.

(10) Patent No.: US 7,563,741 B2
(45) Date of Patent: Jul. 21, 2009

(54) SILICONE COMPOSITION WHICH CAN BE CROSSLINKED INTO AN ELASTOMER BY HYDROSILYLATION IN THE PRESENCE OF CARBENE-BASED METAL CATALYSTS, AND CATALYSTS OF THIS TYPE

(75) Inventors: Oliver Brummer, Berlin (DE); Eric D. Carlson, Cupertino, CA (US); Thomas Crevier, San Jose, CA (US); Yves Giraud, Sainte Foy les Lyon (FR); Anne-Marie La Pointe, Sunnyvale, CA (US); Sébastien Sterin, Lyons (FR)

(73) Assignees: Rhodia Chimie, Aubervilliers (FR); Symyx Technologies, Inc., Santa Clara, CA (US)

( * ) Notice: Subject to any disclaimer, the term of this patent is extended or adjusted under 35 U.S.C. 154(b) by 587 days.

(21) Appl. No.: 10/515,319

(22) PCT Filed: May 23, 2003

(86) PCT No.: PCT/EP02/07457

§ 371 (c)(1),
(2), (4) Date: Sep. 12, 2005

(87) PCT Pub. No.: WO03/099909

PCT Pub. Date: Dec. 4, 2003

(65) Prior Publication Data

US 2006/0173150 A1    Aug. 3, 2006

(51) Int. Cl.
*B01J 31/00* (2006.01)
*B01J 23/74* (2006.01)

(52) U.S. Cl. ............. 502/150; 502/152; 502/155; 502/158; 502/162; 502/185

(58) Field of Classification Search .......... 502/150, 502/325, 155, 158, 162, 185, 152; 528/14, 528/15, 21, 31, 32
See application file for complete search history.

(56) References Cited

U.S. PATENT DOCUMENTS

| | | | |
|---|---|---|---|
| 5,364,921 A * | 11/1994 | Gray et al. ............... | 528/15 |
| 5,728,839 A | 3/1998 | Herrmann et al. | |
| 6,316,380 B1 | 11/2001 | Nolan et al. | |
| 6,362,357 B1 | 3/2002 | Nolan et al. | |
| 6,803,440 B2 * | 10/2004 | Marko et al. ............. | 528/14 |
| 6,815,518 B2 * | 11/2004 | Sterin ..................... | 528/15 |
| 7,019,145 B2 * | 3/2006 | Buisine et al. ........... | 548/101 |
| 7,202,320 B2 * | 4/2007 | George et al. ........... | 528/14 |

FOREIGN PATENT DOCUMENTS

WO     01/42258 A1    6/2001

* cited by examiner

*Primary Examiner*—Michael A Marcheschi
*Assistant Examiner*—James E McDonough
(74) *Attorney, Agent, or Firm*—Buchanan, Ingersoll & Rooney P.C.

(57) ABSTRACT

This invention relates to silicone compositions which can be crosslinked, preferably into elastomers, by hydrosilylation of at least one PolyOrganoSiloxane -A- carrying unsaturated bonds, using at least one polyorganohydrosiloxane —B— in the presence of a carbene-based metal catalyst —C— as defined in the description and which optionally comprises at least one inhibitor -D- of the hydrosilylation reaction.

32 Claims, No Drawings

SILICONE COMPOSITION WHICH CAN BE CROSSLINKED INTO AN ELASTOMER BY HYDROSILYLATION IN THE PRESENCE OF CARBENE-BASED METAL CATALYSTS, AND CATALYSTS OF THIS TYPE

CROSS-REFERENCE TO RELATED APPLICATION

This application is the U.S. national stage of International Appln. No. PCT/EP02/07457, filed May 23, 2002, said application being incorporated by reference herein in its entirety relied upon.

The invention relates to the catalysis of hydrosilylation reactions of ethylenically and/or acetylenically unsaturated compounds (for example, olefins or acetylenic derivatives), in particular those involving polyorganosiloxanes (POSs) carrying Si—H units and POSs carrying Si-(ethylenic or acetylenic unsaturation) units.

More specifically, the invention relates to silicone compositions which can be crosslinked (preferably into elastomers) by hydrosilylation of at least one PolyOrganoSiloxane -A- (POS) carrying unsaturated bonds using at least one polyorganohydrosiloxane —B— in the presence of a metal catalyst —C— and which optionally comprise at least one inhibitor -D- of the hydrosilylation reaction.

Hydrosilylation reactions which make it possible for silicones to crosslink are conventionally catalysed by platinum catalysts (U.S. Pat. No. 2,823,218, U.S. Pat. No. 2,970,150). In practice, to date, the majority of industrial hydrosilylation reactions are catalysed by the Karstedt solution, which is composed of platinum complexes in which the platinum is in the 0 oxidation state.

The very high catalytic activity of this type of catalyst, even at ambient temperature, is a major disadvantage in the context of its use in polyaddition HCEs as the crosslinking of the elastomer begins as soon as all the components are brought into contact.

The document WO 01/42558 discloses in particular metal complexes of use as hydrosilylation catalysts, of formula:

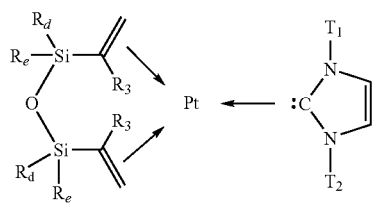

in which:

$R_3$ represents a hydrogen atom; a $(C_1\text{-}C_8)$alkyl group; or a $(C_3\text{-}C_8)$cycloalkyl group;

$T_1$ and $T_2$ are identical and represent $(C_1\text{-}C_8)$alkyl or $(C_3\text{-}C_8)$ cycloalkyl;

$R_d$ and $R_e$ are identical and represent $(C_1\text{-}C_8)$alkyl or $(C_3\text{-}C_8)$ cycloalkyl.

According to this application, the catalysts are employed for the catalysis of the reaction of a compound comprising an unsaturated bond with a compound exhibiting at least one ≡S—H unit.

Patent U.S. Pat. No. 5,728,839 itself also discloses metal/carbene complexes with heterocyclic carbenes; they are described as being able to be of use as catalysts for the hydrogenation or hydroformylation of unsaturated organic compounds. There is no mention of the crosslinking of silicones in this document.

In point of fact, it might be advantageous to have available, in the field of crosslinkable silicones (in particular those which can be crosslinked into elastomers), catalysts which are active under hot conditions and inactive or virtually inactive at ambient temperature. This would make it possible to formulate single-component silicone compositions which can be crosslinked under hot conditions and which are stable on storage for lengthy periods of time at ambient temperature (pot life). Single-component silicone compositions are those which comprise, in the same mixture, all the reactive entities (Si-Vinyl POS/Si-H POS) and the catalyst. Conventionally, crosslinking inhibitors are used to increase the pot life of single-component silicone compositions. Thus, with the Karstedt catalyst, the use of an inhibitor is essential and makes it possible to change, for example, the stability at ambient temperature of an Si-Vinyl POS/Si-H POS composition from 1 min to 24 H.

Objectives

In such a state of the art, one of the essential objectives of the invention is to provide a silicone composition which can be crosslinked by hydrosilylation and which comprises, as catalyst, one or more metal complexes based on heterocyclic carbenes, this catalyst having a low activity at ambient temperature, so as to make possible the preparation of single-component compositions comprising the catalyst and compounds capable of reacting under hot conditions by hydrosilylation of unsaturated units, while being stable at ambient temperature for lengthy periods (e.g. 1 d to a few months).

Another essential objective of the invention is to provide a silicone composition which can be crosslinked by hydrosilylation and which comprises, as catalyst, one or more metal complexes based on heterocyclic carbenes, this composition not being the site, during crosslinking, of isomerization side reactions or of colorations capable of interfering with the hydrosilylation.

Another essential objective of the invention is to provide novel metal complexes based on heterocyclic carbenes which can be used as hydrosilylation catalysts, the latter having to be highly active under hot conditions and inactive or virtually inactive at ambient temperature, so as to be able to formulate single-component silicone compositions which can be crosslinked under hot conditions and which are stable on storage for lengthy periods of time at ambient temperature (pot life), this being achieved with little or no crosslinking inhibitor.

Another essential objective of the invention is to provide a hydrosilylation process and in particular a process for the hydrosilylation of ethylenically and/or acetylenically unsaturated compounds in the presence of a catalyst comprising the novel metal complexes targeted above.

These objectives are achieved by the present invention, which relates, first, to a silicone composition which can be crosslinked by hydrosilylation of at least one PolyOrganoSiloxane -A- (POS) carrying unsaturated bonds [example: ethylenic and/or acetylenic unsaturation(s)] using at least one polyorganohydro-siloxane —B— in the presence of a metal catalyst —C— and which optionally comprises at least one inhibitor -D- of the hydrosilylation reaction;

characterized in that the catalyst —C— comprises at least one compound selected from the products of formula (I):

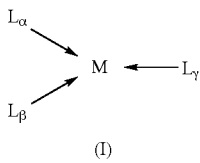

(I)

in which:
M represents a metal chosen from the metals of Group 8 of the Periodic Table as published in the Handbook of Chemistry and Physics, 65th edition, 1984-1985;
$L_\gamma$ represents a carbene of formula (II):

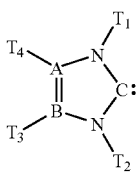

II in which:
A and B, which are identical or different, represent C or N, it being understood that, when A represents N, then $T_4$ does not represent anything and, when B represents N, then $T_3$ does not represent anything;
$T_3$ and $T_4$ independently represent a hydrogen atom; an alkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or else
$T_3$ and $T_4$ can together and with A and B, when the latter each represent a carbon atom, form an aryl;
$T_1$ and $T_2$ independently represent an alkyl group; an alkyl group optionally substituted by alkyl; a perfluorinated alkyl group or an alkyl group optionally substituted by a perfluoroalkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or else
$T_1$ and $T_2$ independently represent a monovalent radical of following formula (V):

$V_1\text{-}V_2$  (V), in which:

$V_1$ is a divalent hydrocarbonaceous radical, preferably an alkylene,
$V_2$ is a monovalent radical chosen from the group of the following substituents:
  alkoxy, —OR° with R° corresponding to hydrogen, alkyl or aryl,
  amine, preferably N(R°)$_2$ with R° corresponding to hydrogen, alkyl or aryl;
$T_1$ and $T_2$ independently represent a monovalent radical of following formula (W):

$W_1\text{-}\omega\text{-}W_2$  (W)

in which:
$W_1$ is a divalent hydrocarbonaceous radical, preferably a linear or branched $C_1$-$C_{10}$ alkylene, which is optionally substituted;

ω represents:
—R$^1$C=CR$^1$—
with R$^1$ corresponding to H or alkyl,
or
—C≡C—;
$W_2$ is a monovalent radical chosen from the group of the following substituents:
R$^2$=alkyl or H;
Si-alkyl or Si-alkoxy, preferably —Si(R$^3$)$_3$ with R$^3$=alkyl;
alcohol, preferably —C(R$^4$)$_2$OH with R$^4$=H or alkyl;
ketone, preferably

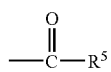

with R$^5$=alkyl;
carboxyl, preferably

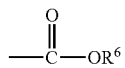

with R$^6$=alkyl;
amide, preferably

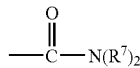

with R$^7$=H or alkyl;
acyl, preferably

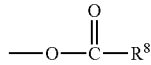

with R$^8$=alkyl;
or else
the substituents $T_1$, $T_2$, $T_3$ and $T_4$ can form in pairs, when they are situated at two adjacent points in the formula (II), a saturated or unsaturated hydrocarbonaceous chain;
and with the condition that at least one substituent $T_1$ and/or $T_2$, which are identical or different, represent(s) a monovalent radical of following formula (V):

$Z_1\text{-}Z_2$  (V)

in which:
$Z_1$ is a divalent hydrocarbonaceous radical, preferably an alkylene,
$Z_2$ is a monovalent radical chosen from:
  a ($C_5$-$C_{30}$)cycloalkyl radical comprising at least one heteroatom in the ring, preferably nitrogen,
  a ($C_6$-$C_{30}$)aryl radical comprising at least one heteroatom in the aromatic ring, preferably nitrogen,
$L_\alpha$ and $L_\beta$ are ligands which are identical to or different from one another and each represent:

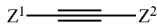
(III.1)

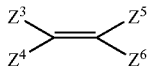
(III.2)

with, in these formulae (III.1) and (III.2):
$Z^1$, $Z^2$, $Z^3$, $Z^4$, $Z^5$ and $Z^6$
each independently representing:
a. hydrogen,
b. a halogen,
c. a cyano,
d. a saturated or unsaturated, electron-withdrawing or non-electron-withdrawing, hydrocarbonaceous group, preferably unsaturated adjacent to the double or triple bond,
e. it being possible for two vicinal $Z^1$ to $Z^6$ groups together to form an electron-withdrawing or non-electron-withdrawing ring which is advantageously other than the carbene $L_\gamma$ of formula (II) and which optionally comprises heteroatoms (preferably O, N or S);
or together form the ligand $L_\delta$ of formula (IV):

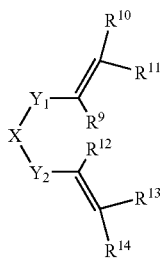
(IV)

in which:
$Y_1$ and $Y_2$ represent, independently of one another, $CR_aR_b$ or $SiR_cR_d$;
X represents O, $NR_e$ or $CR_fR_g$;
$R^{10}$, $R^{11}$, $R^{13}$ and $R^{14}$, which are identical or different, are chosen from a hydrogen atom, an alkyl group or an aryl group optionally substituted by alkyl;
$R^9$, $R^{12}$, $R_a$, $R_b$, $R_c$ and $R_d$ are chosen independently from a hydrogen atom; an alkyl group; an acyl group; an aryl group optionally substituted by alkyl; a cycloalkyl group optionally substituted by alkyl; and an arylalkyl group in which the aryl part is optionally substituted by alkyl;
$R_c$ and $R_d$ are chosen independently from alkyl; aryl optionally substituted by alkyl; cycloalkyl optionally substituted by alkyl; and arylalkyl in which the aryl part is optionally substituted by alkyl; or else
when $Y_1$ and $Y_2$ independently represent $SiR_cR_d$, two $R_c$ groups bonded to two separate silicon atoms together form a chain of formula:

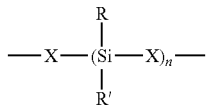

in which n is an integer from 1 to 3; X is as defined above; R and R', which are identical or different, take any one of the meanings given above for $R_e$, it being understood that, when n is 2 or 3, only one silicon atom of the said chain may be substituted by one or two alkenyl or alkynyl groups; or else when $Y_1$ and $Y_2$ independently represent $SiR_cR_d$, two $R_c$ groups bonded to separate silicon atoms together form a saturated hydrocarbonaceous chain, the two $R_c$ groups forming, together with the said silicon atoms and X, a 6- to 10-membered ring; or else when $Y_1$ and $Y_2$ independently represent $CR_aR_b$, two $R_a$ groups bonded to separate carbon atoms together form a saturated hydrocarbonaceous chain, the two $R_a$ groups forming, together with the carbon atoms which carry them and X, a 6- to 10-membered ring; and $R_f$ and $R_g$ represent, independently of one another, a hydrogen atom; an alkyl group; an acyl group; an aryl group optionally substituted by alkyl; a cycloalkyl group optionally substituted by alkyl; an arylalkyl group in which the aryl part is optionally substituted by alkyl; a halogen atom; an alkenyl group; an alkynyl group; or an $SiG_1G_2G_3$ group where $G_1$, $G_2$ and $G_3$ are, independently of one another, alkyl; alkoxy; aryl optionally substituted by alkyl or alkoxy; or arylalkyl in which the aryl part is optionally substituted by alkyl or alkoxy.

The presence of specific metal/heterocyclic carbene complexes in the compositions according to the invention confers great stability on the latter in an ambient atmosphere under standard temperature, humidity and pressure conditions. Such silicone compositions can be stored in the single-component form, in the uncrosslinked state, in an ambient atmosphere, for long periods of time (for example, from 1 to several months). This result is all the more advantageous and surprising since, with some metal/heterocyclic carbene catalysts, it is possible to dispense with the use of crosslinking inhibitors or, at the very least, to use less thereof, which is entirely beneficial economically and with regard to limiting the negative repercussions on the crosslinking of the elastomer and its final qualities.

This stability goes together with the ability which the compositions according to the invention have to crosslink under hot conditions (for example from 100° C.) by hydrosilylation into elastomers of good quality, in particular at the structural and mechanical level. In addition, the kinetics of the reaction are satisfactory.

These single-component silicone compositions, which have a long pot life at ambient temperature, are all the more advantageous because their cost is not prohibitive. This advantage is even more marked when they do not comprise an inhibitor.

The definition of the metal complexes of formula (I) constituting the catalyst —C—, an essential compound of the composition according to the invention, is completed below.

The metals of Group 8 represented by M in the formula (I) are, for example, palladium, platinum or nickel in the zero oxidation state. In practice, M represents platinum in the 0 oxidation state.

The term "alkyl" denotes a saturated, linear or branched, hydrocarbonaceous chain which is optionally substituted (e.g. by one or more alkyls), preferably with from 1 to 10 carbon atoms.

Examples of alkyl groups are in particular methyl, ethyl, isopropyl, n-propyl, tert-butyl, n-butyl or n-pentyl.

The alkyl part of the alkoxy radical is as defined above.

The term "cycloalkyl" is understood to mean a saturated, mono- or polycyclic, preferably mono- or bicyclic, hydrocarbonaceous radical preferably exhibiting from 3 to 10 carbon atoms.

The term "saturated polycyclic hydrocarbonaceous radical" is understood to mean a radical exhibiting two or more rings attached to one another via σ bonds and/or condensed in pairs.

Examples of polycyclic cycloalkyl groups are adamantyl and norbornyl.

Examples of monocyclic cycloalkyl groups are cyclopentyl and cyclohexyl.

The term "perfluorinated alkyl" denotes an alkyl comprising at least one perfluoroalkyl group preferably having the formula:

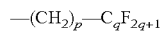

in which p represents 0, 1, 2, 3 or 4; q is an integer from 1 to 10; and $C_qF_{2q+1}$ is linear or branched.

The expression "aryl" denotes a monocyclic or polycyclic, preferably monocyclic or bicyclic, aromatic hydrocarbonaceous group having from 6 to 18 carbon atoms. It should be understood that, in the context of the invention, the term "polycyclic aromatic radical" is understood to denote a radical exhibiting two or more aromatic nuclei condensed (ortho-condensed or ortho- and peri-condensed) with one another.

The said aromatic hydrocarbonaceous ("aryl") group is optionally substituted, for example by one or more $C_1$-$C_3$ alkyls, one or more halogenated hydrocarbonaceous radicals (e.g. $CF_3$), one or more alkoxys (e.g. $CH_3O$) or one or more hydrocarbonaceous radicals comprising one or more ketone units (e.g. $CH_3CO$—).

Mention may be made, as examples of aryl, of the phenyl and naphthyl radicals.

The expression "arylalkyl" denotes an alkyl group as defined above substituted on its hydrocarbonaceous chain by one or more aryl groups, the aryl group being as defined above. Examples thereof are benzyl and triphenylmethyl.

The term "acyl" is understood to denote an $R^o$—CO— group where $R^o$ represents an alkyl as defined above; or else an Ar—CO— group where Ar represents an aryl group as defined above; or else an arylalkyl in which "aryl" and "alkyl" are as defined above and in which the aryl part is optionally substituted, e.g. by an alkyl.

The term "alkenyl" is understood to denote an unsaturated, substituted or unsubstituted, linear or branched, hydrocarbonaceous chain exhibiting at least one olefinic double bond and more preferably a single double bond. Preferably, the alkenyl group exhibits from 2 to 8 carbon atoms, better still from 2 to 6. This hydrocarbonaceous chain optionally comprises at least one heteroatom, such as O, N or S. Preferred examples of alkenyl groups are the allyl and homoallyl groups.

The term "alkynyl" is understood to denote, according to the invention, an unsaturated, substituted or unsubstituted, linear or branched, hydrocarbonaceous chain exhibiting at least one acetylenic triple bond and more preferably a single triple bond. Preferably, the alkynyl group exhibits from 2 to 8 carbon atoms, better still from 2 to 6 carbon atoms. Mention may be made, by way of examples, of the acetylenyl group and the propargyl group. This hydrocarbonaceous chain optionally comprises at least one heteroatom, such as O, N or S.

The expression "does not represent anything" means that the -$T_3$ and -$T_4$ substituents respectively do not exist. This is because, in the formula (II), the nitrogen atom is trivalent, so that, when A or B represents N, the nitrogen atom cannot have an additional substituent.

Preferably, in the carbene ligands of formula (II):

(i) $T_3$ and $T_4$ represent a hydrogen atom or together form a phenyl, and/or (ii) $T_1$ and $T_2$, which are identical or different, represent(s) a monovalent radical of following formula (V):

$$*Z_1\text{-}Z_2 \quad\quad\quad (V)$$

in which:

$Z_1$ is a divalent hydrocarbonaceous radical, preferably an alkylene, $Z_2$ is a monovalent radical chosen from:
  a ($C_5$-$C_{30}$)cycloalkyl radical comprising at least one heteroatom in the ring, preferably nitrogen,
  a ($C_6$-$C_{30}$)aryl radical comprising at least one heteroatom in the aromatic ring, preferably nitrogen, and/or (iii) A and B both represent a carbon atom.

The ligands $L_\alpha$ and $L_\beta$ of the catalyst —C— of formula (I) belonging to the composition according to the invention can independently represent an alkyne of formula (III.1) or an alkene of formula (III.2) substituted by $Z^1$ to $Z^6$ radicals carrying at least one electron-withdrawing unit active with respect to π unsaturation of $L_\alpha$ and $L_\beta$, in order to promote the liganding with the metal M of the complex.

Advantageously, in the formulae (III.1) and (III.2), the electron-withdrawing residues are chosen from the group consisting of:

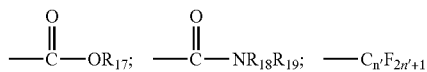

in which:

$R_{17}$, $R_{18}$, $R_{19}$ and $R_{20}$, which are identical or different, are substituted or unsubstituted alkyl, alkenyl or alkynyl and n' is between 1 and 50.

Mention may be made, by way of examples of $Z^1$ to $Z^6$ radicals, of:

those selected from the group consisting of:

and, in the cases where the $Z^1$ and $Z^2$ substituents form in pairs and with the triple bond, in (III.1), a ring Cy1 and where $Z^3$ to $Z^6$ form in pairs, with or without the double bond, in (III.2), a ring Cy2, these rings Cy1 and Cy2 are independently and preferably chosen from the group consisting of the following rings:

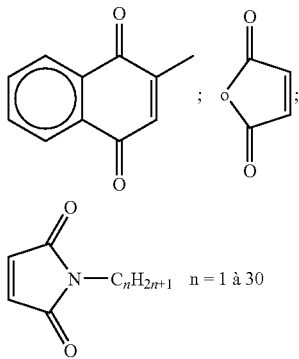

When $L_\alpha$ and $L_\beta$ together form a ligand $L_\delta$ of formula (IV), the latter is preferably of the type of those in which $Y_1$ and $Y_2$ either both represent $CR_aR_b$ or both represent $SiR_cR_d$, so that the said complexes either have the formula (IV.1) or have the formula (IV.2):

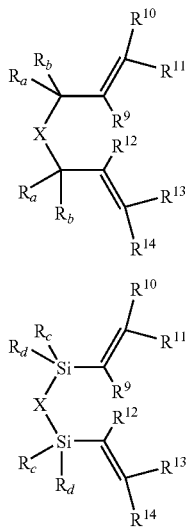

where:

the two $R_a$ groups, the two $R_b$ groups, the two $R_c$ groups and the two $R_d$ groups are identical to one another and $R^9=R^{12}$; $R^{10}=R^{14}$; and $R^{11}=R^{13}$. Preferably, X=O.

According to an alternative form, the two $R_c$ groups in (IV.2) together form (a) either a chain

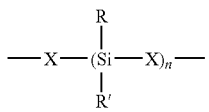

in which n is an integer from 1 to 3; X is as defined above; and R and R', which are identical or different, take any one of the meanings given above for $R_d$, it being understood that, when n is 2 or 3, only one silicon atom of the said chain may be substituted by one or two alkenyl or alkynyl groups;

(b) or a saturated hydrocarbonaceous chain, so that the two $R_c$ substituents form, together with the two silicon atoms which carry them X, a 6- to 10-membered ring, preferably a 6- to 8-membered ring.

In this respect, more detailed and preferred examples of structures $R_c$-$R_c$ are given in Application WO 01/42258, page 7, line 11 to page 9, line 19, under the form "Rd$^1$-Rd$^2$".

In the context of the invention, the expression "independently represent" means that the designated substituents are either identical or different.

Preferred meanings of $R_9$ and $R_{12}$ are in particular a hydrogen atom; an alkyl group; an aryl group optionally substituted by alkyl; and a cycloalkyl group optionally substituted by alkyl.

For example, the diolefinic ligand $L_\delta$ of formula (IV) is symmetrical, that is to say that $R_{10}=R_{14}$; $R_{11}=R_{13}$; $R_9=R_{12}$ and the two groups $Y_1$ and $Y_2$ are either strictly identical to one another, or $Y_1=CR_aR_b$ and $Y_2=CR_aR_b$, or $Y_1=SiR_cR_d$ and $Y_2=SiR_cR_d$.

As regards the catalyst —C— of the composition according to the invention, mention should be made of a first particularly preferred group of metal complexes of following formula (I.1):

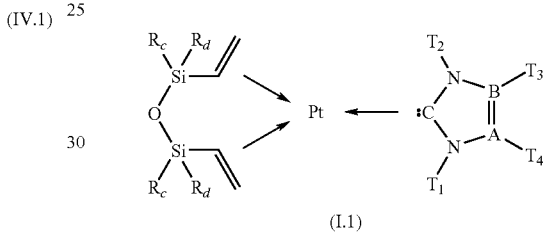

in which:
$T_1$ and $T_2$ are identical and are as defined above;
$T_3$ and $T_4$ are as defined above;
$R_c$ and $R_d$ are as defined above.

A second particularly preferred group of catalysts —C— of the composition according to the invention comprises the metal complexes of following formula (I.2):

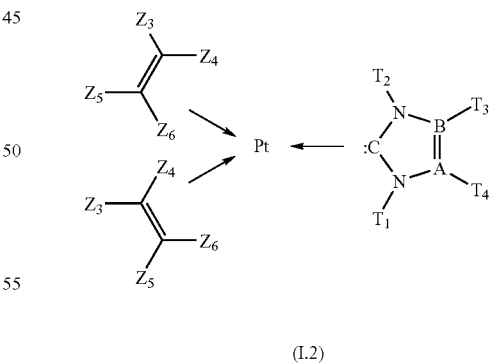

in which:
$T_1$ and $T_2$ are identical and are as defined above;
$T_3$ and $T^4$ are as defined above;
$Z_3$ to $Z_6$ are as defined above.

A third particularly preferred group of catalysts —C— of the composition according to the invention comprises the metal complexes of following formula (I.3):

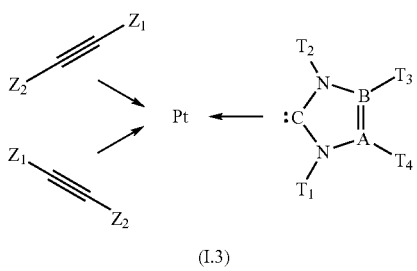

(I.3)

in which:
T$_1$ and T$_2$ are identical and are as defined above;
T$_3$ and T$_4$ are as defined above;
and Z$_1$ and Z$_2$ are as defined above.

In addition to the catalyst —C—, the composition according to the invention comprises the two polyorganosiloxane entities reactive by polyaddition, namely the POS -A- and the POS —B—. The latter are chosen from the POSs composed of siloxyl units of general formula:

$$(R^{20})_x SiO_{(4-x)/2} \tag{I'}$$

and/or of siloxyl units of formula:

$$(R^{21})_y (R^{22})_z SiO_{(4-y-z)/2} \tag{II'}$$

in which formulae the various symbols have the following meanings:
the R$^{20}$ and R$^{22}$ symbols, which are identical or different, each represent a group with a nonhydrolysable hydrocarbonaceous nature, it being possible for this radical to be:
an alkyl or haloalkyl radical having from 1 to 5 carbon atoms and comprising from 1 to 6 chlorine and/or fluorine atoms,
cycloalkyl and halocycloalkyl radicals having from 3 to 8 carbon atoms and comprising from 1 to 4 chlorine and/or fluorine atoms,
aryl, alkylaryl and haloaryl radicals having from 6 to 8 carbon atoms and comprising from 1 to 4 chlorine and/or fluorine atoms,
cyanoalkyl radicals having from 3 to 4 carbon atoms;
the R$^{21}$ symbols, which are identical or different, each represent a hydrogen atom, a C$_2$-C$_6$ alkenyl group, a hydroxyl group, a hydrolysable atom or a hydrolysable group;
x=an integer equal to 0, 1, 2, or 3;
y=an integer equal to 0, 1, 2, or 3;
z=an integer equal to 0, 1 or 2;
the sum y+z is between 1 and 3;
with the condition according to which the Si-alkenyl POS -A- comprises at least one unit R$^{21}$=alkenyl per molecule and the Si—H POS —B— comprises at least one unit R$^{21}$=hydrogen per molecule.

These POSs -A- and —B— are, for example, respectively a polyorganovinylsiloxane and a polyorganohydrosiloxane. The organic substituents, other than the vinyl reactive groups and the hydrogen, are, for example, methyls or phenyls. The hydrogens and the vinyls are carried by siloxyl units M=[R$_3$SiO—] and/or D=[-(R)$_2$SiO—] and/or T=[-(R)SiO—]. These hydrogenated or vinylated units M and D each comprise one or more H or vinyl units, preferably only one.

The number of SiH or SiVi units per molecule is at least equal to 2 and preferably at greater than 2.

This can represent from 0.01% to 10% (preferably 0.1 to 2%) of vinyl group (27 g/mol) by weight for the POS -A- and from 0.001% to 5% (preferably 0.05 to 2%) of hydrogen group (lg/mol) by weight for the POS —B—.

Generally, the POSs -A- and —B— which can be used in the reaction have an average molecular mass of between $1 \times 10^2$ and $1 \times 10^7$ (g/mol).

For the POS -A-, this encompasses in particular, in terms of dynamic viscosity at 25° C., ranges:
of POSs which can be cured under hot conditions (HCE) by polyaddition, having a viscosity at least equal to $1 \times 10^5$ mPa·s, preferably of between $1 \times 10^6$ and $1 \times 10^7$ mPa·s,
and of POSs which can be cured under hot conditions by polyaddition, of liquid silicone elastomer (LSR) type, having a viscosity preferably of between $1 \times 10^5$ and $5 \times 10^5$ mPa·s.

According to a preferred form of the invention, the silicone compositions concerned are POSs which can be cured under hot conditions (HCE) by polyaddition and in which the POSs -A- can have in practice a viscosity at 25° C. of, e.g., $2 \times 10^6$ mPa·s and the POSs —B— of 10 to 5 000 mPa·s (e.g. 300 mPa·s).

In these examples, the viscosity is measured using a Brookfield viscometer according to the directions of the AFNOR Standard NFT 76 106 of May 82.

All the viscosities concerned in the present account correspond to a "Newtonian" dynamic viscosity quantity at 25° C., that is to say the dynamic viscosity which is measured, in a way known per se, at a shear rate gradient which is sufficiently low for the viscosity measured to be independent of the rate gradient.

The composition according to the invention can also comprise a certain number of conventional ingredients in addition to the POSs -A- and —B— and the catalyst —C—, including in particular at least one crosslinking inhibitor -D- capable of slowing down the polyaddition reaction and of making possible the storage of the single-component composition -A-B-C-D- in a not entirely crosslinked state.

The invention consequently relates to silicone compositions comprising at least one inhibitor -D- and in which the catalyst —C— is chosen from metal complexes of formula (I.1), formula (I.2), where Z3 to Z6 are devoid of electron-withdrawing residue(s), and formula (I.3), where Z1 and Z2 are devoid of electron-withdrawing residue(s). These compositions have long storage times (pot lives).

It should be noted that for some catalysts —C—, in particular those comprising a carbene (II) and at least one (preferably two) ligands L$_\alpha$ and L$_\beta$ of formula (III.1) or (III.2), it is not necessary to use an inhibitor.

The invention is consequently also targeted at silicone compositions devoid of inhibitor -D- and in which the catalyst —C— is chosen from metal complexes:
of formula (I.2), where T$_1$, T$_2$, T$_3$, T$_4$, R$_c$ and R$_d$ are as defined above and at least one of the Z$^3$ to Z$^6$ substituents (preferably each substituent) comprises at least one electron-withdrawing residue;
and/or of formula (I.3), where T$_1$, T$_2$, T$_3$ and T$_4$ are as defined above and Z$^1$ and Z$^2$ are devoid of electron-withdrawing residue(s).

These inhibitor-free compositions have, entirely advantageously and unexpectedly, long storage lives (pot lives) in an ambient atmosphere. Cross-linking only occurs under hot conditions. This advantage is a major one economically and with regard to convenience of use and of storage.

Advantageously, the inhibitors -D- (if they are employed) are selected from:

polyorganosiloxanes, advantageously cyclic polyorganosiloxanes, substituted by at least one alkenyl, tetramethylvinyl-tetrasiloxane being particularly preferred,
alkyl, alkenyl or alkynyl maleates, diallyl maleate being particularly preferred,
acetylenic alcohols,
and/or alkyl, alkenyl or alkynyl acetylenedicarboxylates.

Such an inhibitor -D- is present in a proportion of at most 3 000 ppm, preferably in a proportion of 100 to 2 000 ppm, with respect to the total weight of the polyorganosiloxanes -A- and —B—.

Mention may be made, as conventional families of conventional functional additives capable of being employed in the silicone compositions according to the invention, of:
fillers,
hydroxylated POS oils of use as compatibilizer,
adhesion promoters,
adhesion modifiers,
pigments,
additives for stability towards heat, oils or fire (for example, metal oxides).

The fillers optionally provided are preferably inorganic fillers. They can be composed of products chosen from siliceous materials which can act as reinforcing or semi-reinforcing filler.

Reinforcing siliceous fillers are chosen from colloidal silicas, fumed and precipitated silica powders, or their mixture.

Semi-reinforcing siliceous fillers, such as diatomaceous earths or ground quartz, can also be employed.

As regards nonsiliceous inorganic materials, they can be used as semi-reinforcing or bulking inorganic filler.

Examples of these nonsiliceous fillers, which can be used alone or as a mixture, are carbon black, titanium dioxide, aluminium oxide, alumina hydrate, expanded vermiculite, nonexpanded vermiculite, calcium carbonate, zinc oxide, mica, talc, iron oxide, barium sulphate and slaked lime.

Conveniently but without implied limitation, the fillers employed can be a mixture of quartz and silica.

The fillers can be treated with any appropriate product.

It is preferable, by weight, to employ an amount of filler of between 20 and 50, preferably between 25 and 35% by weight, with respect to the combined constituents of the composition.

More generally, the amounts in the compositions according to the invention are standard proportions in the technical field under consideration, it being understood that the targeted application also has to be taken into account.

According to another of its aspects, the present invention relates, as novel products, to the complexes of formula (I) as defined above, of use in particular as catalysts —C—.

The invention additionally relates to any catalytic composition comprising, as active material, one or more metal complexes of formula (I) as defined above.

Such catalysts (in particular hydrosilylation catalysts) have the distinctive characteristic that they can be formed in situ in silicone compositions of the type of those according to the invention, provided that the compositions comprise ligands $L_\alpha$ and $L_\beta$ of formula (III.1) or (III.2), for example as inhibitor -D-. This or these ligands $L_\alpha$ and $L_\beta$ of formula (III.1) or (III.2) are capable of displacing the initial ligands $L_\delta$ from the catalyst —C—. These are latent catalysts. The present invention obviously encompasses this scenario.

Another subject-matter of the invention is a process for the hydrosilylation of olefins or of acetylenic derivatives (for example, hydrosilylation of one or more POSs -A- using one or more POSs —B—), characterized in that it consists in employing the silicone composition as defined above and/or the catalytic composition also described above.

According to an advantageous alternative form in which recourse is had to at least one latent catalyst as described above, use is made of a silicone composition according to the invention as presented above comprising at least one inhibitor -D- which makes possible the in situ formation of at least one metal complex comprising at least one ligand $L_\alpha$ or $L_\beta$ of formula (III.1) or (III.2).

The hydrosilylation reaction can be carried out in a solvent or in the absence of solvent. In an alternative form, one of the reactants can act as solvent: for example, the compound comprising an ethylenic double bond or comprising an acetylenic triple bond.

Appropriate solvents are solvents which are miscible with the compound comprising an Si—H unit.

Under the conditions of the hydrosilylation reaction, the catalyst complex must be dissolved in the reaction medium.

Examples of solvents which can be used for the hydrosilylation are in particular aliphatic hydrocarbons, aromatic hydrocarbons, halogenated aliphatic or aromatic hydrocarbons, or ethers.

The hydrosilylation reaction can be carried out at a temperature of between 15° C. and 300° C., for example between 20 and 240° C.

Generally, the molar ratio of the unsaturations to the Si—H bonds varies between 1:100 and 10:1.

According to the invention, the hydrosilylation reaction is carried out in the presence of a catalytic amount of one or more complexes of formula (I). The term "catalytic amount" is understood to denote less than one molar equivalent of a metal choosen from the metals of group 8 with respect to the amount of unsaturations present in the reaction medium.

Generally, it is sufficient to introduce, into the reaction medium, less than 1 000 ppm, preferably less than 100 ppm, better still less than 50 ppm, of the metal of group 8, calculated with respect to the total mass of the unsaturated compound and of the compound comprising Si—H units.

As regards the preparation of the composition according to the invention, it relates to employing and mixing the compounds -A-, —B—, —C—, optionally -D- and one or more other conventional additives.

The mixing operations are entirely within the scope of a person skilled in the art.

The POSs -A- and —B—, the inhibitors -D- and the other conventional additives, such as fillers, are commodities fully available/accessible to a person skilled in the art.

As regards the metal complexes (I) forming the catalysts —C—, it has been seen above that the catalysts —C— comprising complexes:

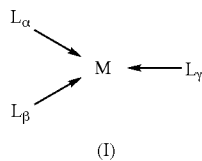

(I)

with $L_\alpha$ and/or $L_\beta$ of formula (III.1) or (III.2), can be obtained from complexes (I) in which $L_\gamma$ is of formula (II) and $L_\alpha$ and $L_\beta$ are of formula (IV), the latter being displaced in situ by inhibitors -D- of formula (III.1) or (III.2).

These complexes (I) in which $L_\gamma$ is of formula (II) and $L_\alpha$ and $L_\beta$ are of formula (IV) are prepared conventionally, for example from known complexes of the state of the art, by ligand exchange, that it to say by addition of the appropriate carbene of formula (II) to a metal complex of the metal M in solution, denoted precursor complex.

Appropriate precursor complexes are, for example, the Karstedt complex.

The complexes of formula (I) are generally prepared from precursor complexes exhibiting, as ligand, at least one diolefinic compound of formula (IV.P):

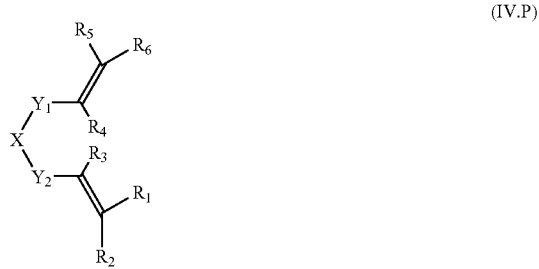

(IV.P)

in which $R_1$, $R_2$, $R_3$, $R_4$, $R_5$, $R_6$, X, $Y_1$ and $Y_2$ are as defined above for the formula (I).

These ligands are either commercially available or are easily prepared by a person skilled in the art from commercial compounds. In this respect, reference may be made to the information given in Application WO 01/42258, more particularly page 15, line 1 to page 18, line 14.

The carbenes of formula (II) can be prepared by deprotonation of imidazolium salts, of tetrazolium salts, of triazolium salts or of pyrazolium salts, according to the situation, under the action of a base.

These reactions can be represented schematically as follows:

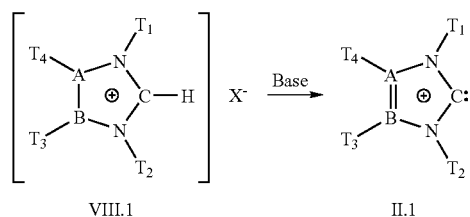

VIII.1　　　　　II.1

In these reaction schemes, $T_1$, $T_2$, $T_3$, $T_4$, A and B are as defined above for the formula (I) and $X^-$ represents an anion.

The nature of the anion $X^-$ is not critical according to the invention. The anion $X^-$ is the anion derived from an organic or inorganic Brönsted acid (protic acid). The anion $X^-$ is usually derived from an acid exhibiting a $pK_a$ of less than 6. Preferably, $X^-$ derives from an acid with a $pK_a$ of less than 4, better still of less than 2. The $pK_a$ values concerned with here are the $pK_a$ values of the acids as measured in water.

Examples of acids are sulphonic acids and phosphonic acids.

Mention will be made, as sulphonic acid, of benzenesulphonic acid and mention will be made, as phosphonic acid, of phenylphosphonic acid.

According to the invention, the anions $X^-$ derived from the acids HCl, HBr, $H_2SO_4$, $HBF_4$ and $H_3PO_4$ are more particularly preferred.

The bases which can be used for the deprotonation of the salts of formula (VIII.1) are strong bases chosen from alkali metal hydrides, alkali metal carboxylates, alkali metal alkoxides and alkali metal amides.

Examples of appropriate bases are therefore sodium hydride, sodium methoxide, potassium tert-butoxide, lithium diisopropylamide and their mixtures.

The deprotonation reaction is preferably carried out in a solvent capable of at least partially dissolving the starting salt of formula (VIII.1) and the other reactants.

The nature of the solvent also depends on the strength of the base. This is because, in the case of a strong base and of particularly reactive starting salts, it may be necessary to operate at a low temperature.

Generally, the reaction temperature is between −78° C. and 40° C., preferably between −50 and 30° C., better still between −40 and 25° C., for example between −30 and 20° C.

Solvents which can be used in the process for the preparation of the carbenes are cyclic or noncyclic ethers.

Other preparation methods suitable for the synthesis of the carbenes of formula (II) are shown in Application WO 01/42258.

According to a particularly preferred embodiment of the invention, the metal complex of the invention has the formula:

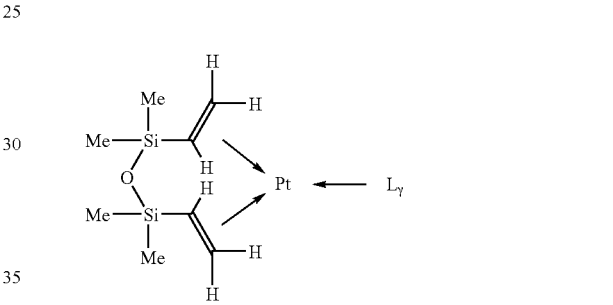

in which $L_\gamma$ is as defined above.

A simple method for the preparation of this complex consists in reacting the carbene L with the "conventional" Karstedt catalyst. This reaction can be carried out in bulk or in a solvent.

Examples of appropriate solvents are cyclic or noncyclic ethers, amides and aromatic hydrocarbons. The reaction temperature usually varies between 10 and 50° C. It is desirable to carry out the reaction in the presence of a slight excess of carbene with respect to the platinum.

Another advantageous preparation process consists in bringing together:

at least one salt of formula (VIII):

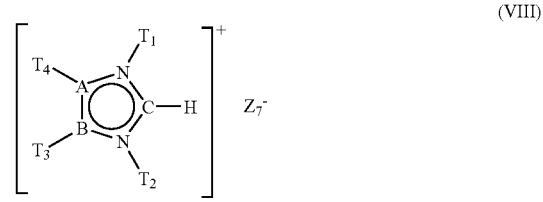

(VIII)

in which:

A, B, $T_1$, $T_2$, $T_3$ and $T_4$ are as defined above;

$Z_7$ independently represents an anion derived from a Brönsted acid (protic acid), at least one appropriate precursor complex of formula (IV.P), at least one solvent (selected in particular from those mentioned above),
and at least one base (selected in particular from those mentioned above).

In this respect, a detailed description of the latter process is shown in French Application No. 01/07473, filed on 7 Jun. 2001.

The catalysts thus prepared can be used in hydrosilylation reactions. They make possible homogeneous catalysis of the reaction.

They also give access to single-component silicone compositions, preferably of polyaddition HCE type, exhibiting much longer pot lives than those prepared with conventional platinum-based catalysts, while using only very little or nothing in the way of inhibitors -D-.

The invention is illustrated in the light of the following examples.

EXAMPLES

The Pt-Carbene complexes used in the examples have the structures described below:

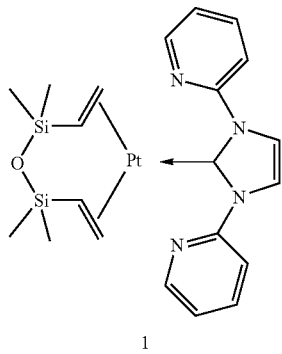

1

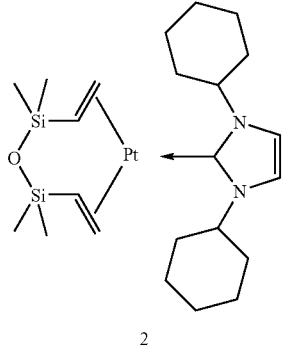

2

1. Synthesis of the Complex 2

The complex 2 was prepared according to the process disclosed in the document WO 01/42558.

2. Synthesis of the Complex 1

1,3-Bis(2-pyridyl)imidazolium chloride, used for the preparation of the complex 1, is synthesized according to the procedure described in the journal Organometallics, 2000, 19, 5113.

0.78 g of 1,3-bis(2-pyridyl)imidazolium chloride (3 mmol) and then 4.66 g of a Karstedt catalyst solution comprising 11.3% of Pt by weight (2.7 mmol of Pt) are introduced into a 250 ml reactor dried beforehand in an oven. 100 ml of anhydrous THF are subsequently added. 3.0 ml of 1M solution of t-BuOK in THF (3 mmol) are then injected over 30 min at 0° C.

The reaction mixture is stirred for an additional hour and then filtered and purified (conventional purification method).

3. Preparation of Crosslinkable Silicone Elastomer Composition

Each composition was prepared according to the following procedure:

An amount of catalyst equivalent to 67 ppm of Pt (calculated with respect to the total mass of vinylsiloxane oil and of hydrosiloxane oil) is dissolved in a few µl of toluene. 10 parts of an α,ω-vinylsiloxane oil, with a viscosity equal to 230 mPa·s and comprising 0.61% by mass of vinyl groups, are added to the solution. In example 3.1 no additional inhibitor is added. In example 3.2 a quantity of inhibitor (3,7,11-trimethyldodecyn-1-ol=TMDDO) is then added, if appropriate (Example 3.2), to produce the desired inhibitor/Pt molar ratio.

After rapid stirring, 2.7 parts of a hydrosiloxane oil, with a viscosity equal to 300 mPa·s and comprising 0.17% by mass of hydrogen, are added.

The DSC analyses of the preceding formulations are described below:

| | Catalyst | Inhibitor/Pt | Temp. Beginning (° C.) | Temp. End (° C.) | Peak of the exotherm (° C.) | Gelling time at 25° C. |
|---|---|---|---|---|---|---|
| Example | | | | | | |
| 3.1 | 1 | / | 106 | 122 | 114 | 30 days |
| 3.2 | 1 | 60 | 150 | 163 | 154 | >15 weeks |
| Counter-example | | | | | | |
| 1 | 2 | / | 95 | 123 | 107 | 1 day |
| 2 | 2 | 60 | 152 | 177 | 164 | 13 weeks |

The DSC curves and the gelling time at 25° C. show that the claimed complexes exhibit a satisfactory activity and result in more stable silicone compositions which can be crosslinked into elastomers.

What is claimed is:

1. A silicone composition which is crosslinkable by hydrosilylation, said composition comprising at least one PolyOrganoSiloxane -A- (POS) carrying ethylenic and/or acetylenic unsaturation(s), at least one polyorganohydrosiloxane —B—, a metal catalyst —C— and optionally at least one inhibitor -D- of the hydrosilylation reaction; said catalyst —C— comprising at least one compound having the formula (I):

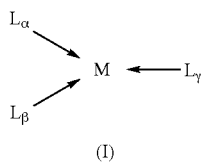

(I)

in which:

M represents a metal of Group 8 of the Periodic Table;

$L_\gamma$ represents a carbene of formula (II):

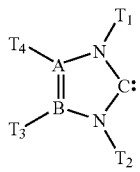
(II)

in which:
A and B, which are identical or different, represent C or N, it being understood that, when A represents N, then $T_4$ does not represent anything and, when B represents N, then $T_3$ does not represent anything;

$T_3$ and $T_4$ independently represent a hydrogen atom; an alkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or $T_3$ and $T_4$ can together with A and B, when the latter each represent a carbon atom, form an aryl;

$T_1$ and $T_2$ independently represent an alkyl group; an alkyl group optionally substituted by alkyl; a perfluorinated alkyl group or an alkyl group optionally substituted by a perfluoroalkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or $T_1$ and $T_2$ independently represent a monovalent radical of following formula (V):

$$V_1-V_2 \quad (V)$$

in which:
$V_1$ is a divalent hydrocarbonaceous radical,
$V_2$ is a monovalent radical selected from the group consisting of the following substituents:
alkoxy, $-OR^o$ wherein $R^o$ is hydrogen, alkyl or aryl, and amine;

$T_1$ and $T_2$ independently represent a monovalent radical of following formula (W):

$$W_1-\omega-W_2 \quad (W)$$

in which:
$W_1$ is a divalent hydrocarbonaceous radical;
$\omega$ represents:
$-R^1C=CR^1-$ wherein $R^1$ is H or alkyl, or
$-C\equiv C-$;
$W_2$ is a monovalent radical selected from the group consisting of the following substituents:
$R^2$, which is alkyl or H;
Si-alkyl or Si-alkoxy;
alcohol;
ketone;
carboxyl;
amide; and
acyl; or the substituents $T_1$, $T_2$, $T_3$ and $T_4$ form in pairs, when they are situated at two adjacent points in the formula (II), a saturated or unsaturated hydrocarbonaceous chain;

and with the condition that at least one substituent $T_1$ and/or $T_2$, which are identical or different, represent(s) a monovalent radical of following formula (V):

$$Z_1-Z_2 \quad (V)$$

in which:
$Z_1$ is a divalent hydrocarbonaceous radical, and
$Z_2$ is a monovalent radical selected from the group consisting of:
a $(C_5-C_{30})$cycloalkyl radical having at least one heteroatom in the ring, and
a $(C_6-C_{30})$aryl radical having at least one heteroatom in the aromatic ring, $L_\alpha$ and $L_\beta$ are ligands which are identical to or different from each other and each represent:

$$Z^1=Z^2 \quad (III.1)$$

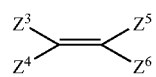
(III.2)

wherein, in these formulae (III.1) and (III.2):
$z^1$, $z^2$, $Z^3$, $Z^4$, $Z^5$ and $Z^6$ each independently represent:
hydrogen,
halogen,
cyano, or
a saturated or unsaturated, electron-withdrawing or non-electron-withdrawing, hydrocarbonaceous group,
or two vicinal $Z_1$ to $Z_6$ groups together form an electron-withdrawing or non-electron-withdrawing ring which optionally comprises heteroatoms;

or $L_\alpha$ and $L_\beta$ together form the ligand $L_\delta$ of formula (IV):

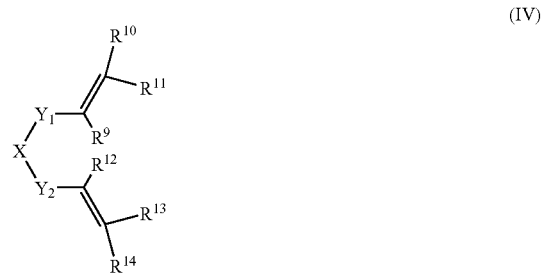
(IV)

in which:
$Y_1$ and $Y_2$ represent, independently of each other, $CR_aR_b$ or $SiR_cR_d$;
X represents O, $NR_e$ or $CR_fR_g$;
$R^{10}$, $R^{11}$, $R^{13}$ and $R^{14}$, which are identical or different, are selected from the group consisting of a hydrogen atom, an alkyl group and an aryl group optionally substituted by alkyl;
$R^9$, $R^{12}$, $R_a$, $R_b$ and $R_e$ are selected independently from the group consisting of a hydrogen atom; an alkyl group; an acyl group; an aryl group optionally substituted by alkyl; a cycloalkyl group optionally substituted by alkyl; and an arylalkyl group in which the aryl part is optionally substituted by alkyl;
$R_c$ and $R_d$ are selected independently from the group consisting of alkyl; aryl optionally substituted by alkyl; cycloalkyl optionally substituted by alkyl; and arylalkyl in which the aryl part is optionally substituted by alkyl; or when $Y_1$ and $Y_2$ independently represent $SiR_cR_d$, two $R_c$ groups bonded to two separate silicon atoms together form a chain of the formula:

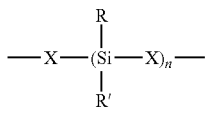

in which n is an integer from 1 to 3; X is as defined above; R and R', which are identical or different, have any one of the meanings given above for $R_e$, it being understood that, when n is 2 or 3, only one silicon atom of the said chain may be substituted by one or two alkenyl or alkynyl groups; or when $Y_1$ and $Y_2$ independently represent $SiR_cR_d$, two $R_c$ groups bonded to separate silicon atoms together form a saturated hydrocarbonaceous chain, the two $R_c$ groups forming, together with the said silicon atoms and X, a 6- to 10-membered ring; or when $Y_1$ and $Y_2$ independently represent $CR_aR_b$, two $R_a$ groups bonded to separate carbon atoms together form a saturated hydrocarbonaceous chain, the two $R_a$ groups forming, together with the carbon atoms which carry them and X, a 6- to 10-membered ring; and $R_f$ and $R_g$ represent, independently of each other, a hydrogen atom; an alkyl group; an acyl group; an aryl group optionally substituted by alkyl;

a cycloalkyl group optionally substituted by alkyl; an arylalkyl group in which the aryl part is optionally substituted by alkyl; a halogen atom; an alkenyl group; an alkynyl group; or an $SiG_1G_2G_3$ group where $G_1$, $G_2$ and $G_3$ are, independently of one another, alkyl; alkoxy; aryl optionally substituted by alkyl or alkoxy; or arylalkyl in which the aryl part is optionally substituted by alkyl or alkoxy.

2. A composition according to claim 1, wherein M is Pt, Pd or Ni in the zero oxidation state.

3. A composition according to claim 1, wherein in the formula (II):

$T_3$ and $T_4$ represent a hydrogen atom or together form phenyl, and/or only one of $T_1$ or and $T_2$ represents $(C_1—C_8)$alkyl or $(C_3—C_8)$cycloalkyl, and/or A and B both represent a carbon atom.

4. A composition according to claim 1, wherein in formulae (III.1) and (III.2), the electron-withdrawing groups are selected from the group consisting of:

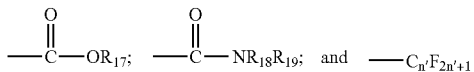

in which:

$R_{17}$, $R_{18}$, $R_{19}$ and $R_{20}$ are each a substituted or unsubstituted alkyl, alkenyl or alkynyl and n' is between 1 and 50.

5. A composition according to claim 1, wherein:

$Z_1$, $Z_2$, $Z_3$, $Z_4$, $Z_5$ and $Z_6$ are selected from the group consisting of $—COOCH_3$, $—COOCH_2CH_3$, $—CONC_{12}H_{25}$ and $—CN$;

or, wherein, when the $Z_1$ and $Z_2$ substituents form in pairs and with the triple bond, in (III.1), a ring Cy1 or wherein when $Z_3$ to $Z_6$ form in pairs, with or without the double bond, in (III.2), a ring Cy2, said rings Cy1 and Cy2 are independently selected from the group consisting of:

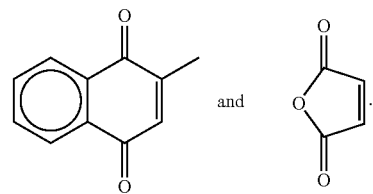

6. A composition according to claim 1, wherein $L_\alpha$ and $L_\beta$ together form a ligand $L_\delta$ of formula (IV) in which $Y_1$ and $Y_2$ either both represent $CR_aR_b$ or both represent $SiR_cR_d$, so that the complexes have the formula (IV.1) or the formula (IV.2):

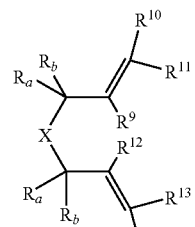

(IV.1)

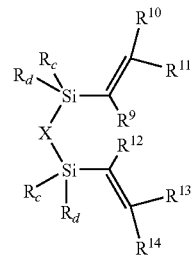

(IV.2)

wherein the two $R_a$ groups, the two $R_b$ groups, the two $R_c$ groups and the two $R_d$ groups are identical to one another and $R^9 =R_{12}$; $R_{10} =R_{14}$; and $R_{11} =R_{13}$.

7. A composition according claim 1, wherein the catalyst —C— has the formula (I.1):

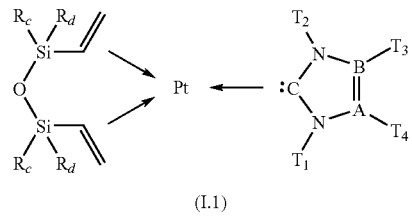

(I.1)

in which:

$T_1$ and $T_2$ are identical and are as defined in claim 13;
$T_3$ and $T_4$ are as defined in claim 1; and
and $R_c$ and $R_d$ are as defined in claim 13.

8. A composition according to claim 1, wherein the POSs -A- and —B— are chosen from those composed of siloxyl units of the formula:

 (I')

and/or of siloxyl units of the formula:

  (II')

in which formulae the symbols have the following meanings:
  $R_{20}$ and $R_{22}$, which are identical or different, each represent a group with a nonhydrolyzable hydrocarbonaceous nature which is:
    an alkyl or haloalkyl radical having from 1 to 5 carbon atoms and having from 1 to 6 chlorine and/or fluorine atoms,
    a cycloalkyl or halocycloalkyl radical having from 3 to 8 carbon atoms and having from 1 to 4 chlorine and/or fluorine atoms,
    an aryl, alkylaryl or haloaryl radical having from 6 to 8 carbon atoms and having from 1 to 4 chlorine and/or fluorine atoms, or
    a cyanoalkyl radical having from 3 to 4 carbon atoms;
  $R_{21}$ represents a hydrogen atom, a $C_2$—$C_6$ alkenyl group, a hydroxyl group, a hydrolyzable atom or a hydrolyzable group, provided that when there are multiple $R_{21}$ groups, they are identical or different;
  x is an integer equal to 0,1, 2, or 3;
  y is an integer equal to 0,1, 2, or 3;
  z is an integer equal to 0, 1 or 2;
  and the sum y+z is from 1 to 3 inclusive;
  with the condition that the Si-alkenyl POS -A- comprises at least one unit $R^{21}$=alkenyl per molecule and the Si—H POS —B— comprises at least one unit $R^{21}$=hydrogen per molecule.

9. The composition according to claim 1, wherein $V_1$ is alkylene and, when $V_2$ is an amine, it has the formula $N(R_o)_2$ wherein $R_o$ is hydrogen, alkyl or aryl.

10. The composition according to claim 1, wherein $W_1$ is linear or branched $C_1$—$C_{10}$ alkylene, which is optionally substituted.

11. The composition according to claim 1, wherein $W_2$ is alkyl, H, —Si$(R_3)_3$ wherein $R_3$ is alkyl, C$(R_4)_2$OH wherein $R_4$ is H or alkyl, —C(O)$R_5$ wherein $R_5$ is alkyl, —C(O)O$R_6$ wherein $R_6$ is alkyl, —C(O)N$(R_7)_2$ wherein $R_7$ is H or alkyl, or —OC(O)$R_8$ wherein $R_8$ is alkyl.

12. The composition according to claim 1, wherein in formula (V), $Z_1$ is alkylene and $Z_2$ is ($C_5$—$_{30}$)cycloalkyl having at least one nitrogen atom in the ring or ($C_6$—$C_{30}$)aryl having at least one nitrogen atom in the aromatic ring.

13. The composition according to claim 1, wherein in formula (III.1) and (III.2), when $Z_1$, $Z_2$, $Z_3$, $Z_4$, $Z_5$ and/or $Z_6$ is an unsaturated electron-withdrawing or non-electron-withdrawing, hydrocarbonaceous group, it is unsaturated adjacent to the double or triple bond.

14. The composition according to claim 1, wherein in formulae (III.1) and (III.2), when two vicinal $Z_1$ to $Z_6$ groups together form an electron-withdrawing or non-electron-withdrawing ring, said ring is other than the carbene $L_\gamma$ of formula (II) and optionally has heteroatoms selected from the group consisting of O, N and S.

15. The composition according to claim 2, wherein M is platinum in the zero oxidation state.

16. The composition according to claim 3, wherein only one of $T_1$ and $T_2$ represents methyl, n-propyl, n-pentyl, cyclohexyl, adamantyl, allyl, methallyl, propargyl or homopropargyl.

17. The composition according to claim 6, wherein X in formula (IV.1) and (IV.2) is an oxygen atom.

18. The composition according to claim 1, wherein the POSs -A- and —B— are chosen from those composed of siloxyl units of the formula:

  (I')

and/or of siloxyl units of the formula:

  (II')

in which formulae the symbols have the following meanings:
  $R_{20}$ and $R_{22}$, which are identical or different, each represent a group with a nonhydrolyzable hydrocarbonaceous nature which is:
    an alkyl or haloalkyl radical having from 1 to 5 carbon atoms and having from 1 to 6 chlorine and/or fluorine atoms,
    a cycloalkyl or halocycloalkyl radical having from 3 to 8 carbon atoms and having from 1 to 4 chlorine and/or fluorine atoms,
    an aryl, alkylaryl or haloaryl radical having from 6 to 8 carbon atoms and having from 1 to 4 chlorine and/or fluorine atoms, or
    a cyanoalkyl radical having from 3 to 4 carbon atoms;
  $R_{21}$ represents a hydrogen atom, a $C_2$—$C_6$ alkenyl group, a hydroxyl group, a hydrolyzable atom or a hydrolyzable group, provided that when there are multiple $R_{21}$ groups, they are identical or different;
  x is an integer equal to 0,1, 2, or 3;
  y is an integer equal to 0,1, 2, or 3;
  z is an integer equal to 0, 1 or 2;
  and the sum y+z is from 1 to 3 inclusive;
  with the condition that the Si-alkenyl POS -A- comprises at least one unit $R^{21}$=alkenyl per molecule and the Si—H POS —B— comprises at least one unit $R^{21}$=hydrogen per molecule.

19. The composition according to claim 2, wherein the POSs -A- and —B— are chosen from those composed of siloxyl units of the formula:

  (I')

and/or of siloxyl units of the formula:

  (II')

in which formulae the symbols have the following meanings:
  $R^{20}$ and $R^{22}$, which are identical or different, each represent a group with a nonhydrolyzable hydrocarbonaceous nature which is:
    an alkyl or haloalkyl radical having from 1 to 5 carbon atoms and having from 1 to 6 chlorine and/or fluorine atoms,
    a cycloalkyl or halocycloalkyl radical having from 3 to 8 carbon atoms and having from 1 to 4 chlorine and/or fluorine atoms,
    an aryl, alkylaryl or haloaryl radical having from 6 to 8 carbon atoms and having from 1 to 4 chlorine and/or fluorine atoms, or
    a cyanoalkyl radical having from 3 to 4 carbon atoms;
  $R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
  x is an integer equal to 0, 1, 2, or 3;
  y is an integer equal to 0, 1, 2, or 3;
  z is an integer equal to 0, 1 or 2;
  and the sum y+z is from 1 to 3 inclusive;
  with the condition that the Si-alkenyl POS -A- comprises at least one unit $R^{21}$=alkenyl per molecule and the Si—H POS —B— comprises at least one unit $R^{21}$=hydrogen per molecule.

20. The composition according to claim 3, wherein the POSs -A- and —B— are chosen from those composed of siloxyl units of the formula:

  (I')

and/or of siloxyl units of the formula:

$(R^{21})_y(R^{22})_z SiO_{(4-y-z)/2}$ (II')

in which formulae the symbols have the following meanings:
$R^{20}$ and $R^{22}$, which are identical or different, each represent a group with a nonhydrolyzable hydrocarbonaceous nature which is:
an alkyl or haloalkyl radical having from 1 to 5 carbon atoms and having from 1 to 6 chlorine and/or fluorine atoms,
a cycloalkyl or halocycloalkyl radical having from 3 to 8 carbon atoms and having from 1 to 4 chlorine and/or fluorine atoms,
an aryl, alkylaryl or haloaryl radical having from 6 to 8 carbon atoms and having from 1 to 4 chlorine and/or fluorine atoms, or
a cyanoalkyl radical having from 3 to 4 carbon atoms;
$R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
x is an integer equal to 0, 1, 2, or 3;
y is an integer equal to 0, 1, 2, or 3;
z is an integer equal to 0, 1 or 2;
and the sum y+z is from 1 to 3 inclusive;
with the condition that the Si-alkenyl POS -A- comprises at least one unit $R^{21}$=alkenyl per molecule and the Si—H POS —B— comprises at least one unit $R^{21}$=hydrogen per molecule.

21. The composition according to claim 4, wherein the POSs -A- and —B— are chosen from those composed of siloxyl units of the formula:

$(R^{20})_x SiO_{(4-x)/2}$ (I')

and/or of siloxyl units of the formula:

$(R^{21})_y(R^{22})_z SiO_{(4-y-z)/2}$ (II')

in which formulae the symbols have the following meanings:
$R^{20}$ and $R^{22}$, which are identical or different, each represent a group with a nonhydrolyzable hydrocarbonaceous nature which is:
an alkyl or haloalkyl radical having from 1 to 5 carbon atoms and having from 1 to 6 chlorine and/or fluorine atoms,
a cycloalkyl or halocycloalkyl radical having from 3 to 8 carbon atoms and having from 1 to 4 chlorine and/or fluorine atoms,
an aryl, alkylaryl or haloaryl radical having from 6 to 8 carbon atoms and having from 1 to 4 chlorine and/or fluorine atoms, or
a cyanoalkyl radical having from 3 to 4 carbon atoms;
$R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
x is an integer equal to 0, 1, 2, or 3;
y is an integer equal to 0, 1, 2, or 3;
z is an integer equal to 0, 1 or 2;
and the sum y+z is from 1 to 3 inclusive;
with the condition that the Si-alkenyl POS -A- comprises at least one unit $R^{21}$=alkenyl per molecule and the Si—H POS —B— comprises at least one unit $R^{21}$=hydrogen per molecule.

22. The composition according to claim 5, wherein the POSs -A- and —B— are chosen from those composed of siloxyl units of the formula:

$(R^{20})_x SiO_{(4-x)/2}$ (I')

and/or of siloxyl units of the formula:

$(R^{21})_y(R^{22})_z SiO_{(4-y-z)/2}$ (II')

in which formulae the symbols have the following meanings:
$R^{20}$ and $R^{22}$, which are identical or different, each represent a group with a nonhydrolyzable hydrocarbonaceous nature which is:
an alkyl or haloalkyl radical having from 1 to 5 carbon atoms and having from 1 to 6 chlorine and/or fluorine atoms,
a cycloalkyl or halocycloalkyl radical having from 3 to 8 carbon atoms and having from 1 to 4 chlorine and/or fluorine atoms,
an aryl, alkylaryl or haloaryl radical having from 6 to 8 carbon atoms and having from 1 to 4 chlorine and/or fluorine atoms, or
a cyanoalkyl radical having from 3 to 4 carbon atoms;
$R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
x is an integer equal to 0, 1, 2, or 3;
y is an integer equal to 0, 1, 2, or 3;
z is an integer equal to 0, 1 or 2;
and the sum y+z is from 1 to 3 inclusive;
with the condition that the Si-alkenyl POS -A- comprises at least one unit $R^{21}$=alkenyl per molecule and the Si—H POS —B— comprises at least one unit $R^{21}$=hydrogen per molecule.

23. The composition according to claim 6, wherein the POSs -A- and —B— are chosen from those composed of siloxyl units of the formula:

$(R^{20})_x SiO_{(4-x)/2}$ (I')

and/or of siloxyl units of the formula:

$(R^{21})_y(R^{22})_z SiO_{(4-y-z)/2}$ (II')

in which formulae the symbols have the following meanings:
$R^{20}$ and $R^{22}$, which are identical or different, each represent a group with a nonhydrolyzable hydrocarbonaceous nature which is:
an alkyl or haloalkyl radical having from 1 to 5 carbon atoms and having from 1 to 6 chlorine and/or fluorine atoms,
a cycloalkyl or halocycloalkyl radical having from 3 to 8 carbon atoms and having from 1 to 4 chlorine and/or fluorine atoms,
an aryl, alkylaryl or haloaryl radical having from 6 to 8 carbon atoms and having from 1 to 4 chlorine and/or fluorine atoms, or
a cyanoalkyl radical having from 3 to 4 carbon atoms;
$R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
x is an integer equal to 0, 1, 2, or 3;
y is an integer equal to 0, 1, 2, or 3;
z is an integer equal to 0, 1 or 2;
and the sum y+z is from 1 to 3 inclusive;
with the condition that the Si-alkenyl POS -A- comprises at least one unit $R^{21}$=alkenyl per molecule and the Si—H POS —B— comprises at least one unit $R^{21}$=hydrogen per molecule.

24. The composition according to claim 7, wherein the POSs -A- and —B— are chosen from those composed of siloxyl units of the formula:

$(R^{20})_x SiO_{(4-x)/2}$ (I')

and/or of siloxyl units of the formula:

$$(R^{21})_y(R^{22})_z SiO_{(4y-z)/2} \quad (II')$$

in which formulae the symbols have the following meanings:
$R^{20}$ and $R^{22}$, which are identical or different, each represent a group with a nonhydrolyzable hydrocarbonaceous nature which is:
  an alkyl or haloalkyl radical having from 1 to 5 carbon atoms and having from 1 to 6 chlorine and/or fluorine atoms,
  a cycloalkyl or halocycloalkyl radical having from 3 to 8 carbon atoms and having from 1 to 4 chlorine and/or fluorine atoms,
  an aryl, alkylaryl or haloaryl radical having from 6 to 8 carbon atoms and having from 1 to 4 chlorine and/or fluorine atoms, or
  a cyanoalkyl radical having from 3 to 4 carbon atoms;
$R^{21}$ represents a hydrogen atom, a $C_2$—$C_6$ alkenyl group, a hydroxyl group, a hydrolyzable atom or a hydrolyzable group, provided that when there are multiple $R^{21}$ groups, they are identical or different;
x is an integer equal to 0, 1, 2, or 3;
y is an integer equal to 0, 1, 2, or 3;
z is an integer equal to 0, 1 or 2;
and the sum y+z is from 1 to 3 inclusive;
with the condition that the Si-alkenyl POS -A- comprises at least one unit $R^{21}$=alkenyl per molecule and the Si—H POS —B— comprises at least one unit $R^{21}$=hydrogen per molecule.

25. A metal complex or catalyst comprising at least one compound having the formula (I):

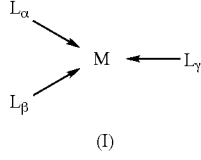

(I)

in which:
M represents a metal of Group 8 of the Periodic Table;
$L_\gamma$ represents a carbene of formula (II):

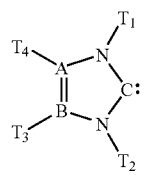

(II)

in which:
A and B, which are identical or different, represent C or N, it being understood that, when A represents N, then $T_4$ does not represent anything and, when B represents N, then $T_3$ does not represent anything;
$T_3$ and $T_4$ independently represent a hydrogen atom; an alkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or
$T_3$ and $T_4$ can together and with A and B, when the latter each represent a carbon atom, form an aryl;

$T_1$ and $T_2$ independently represent an alkyl group; an alkyl group optionally substituted by alkyl; a perfluorinated alkyl group or an alkyl group optionally substituted by a perfluoroalkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or
$T_1$ and $T_2$ independently represent a monovalent radical of following formula (V):

$$V_1—V_2 \quad (V)$$

in which:
$V_1$ is a divalent hydrocarbonaceous radical,
$V_2$ is a monovalent radical selected from the group consisting of the following substituents:
  alkoxy, —$OR^o$ wherein $R^o$ is hydrogen, alkyl or aryl, and amine;
$T_1$ and $T_2$ independently represent a monovalent radical of following formula (W):

$$W_1—\omega—W_2 \quad (W)$$

in which:
$W_1$ is a divalent hydrocarbonaceous radical;
$\omega$ represents:
  —$R^1C$=$CR^1$— wherein $R^1$ is H or alkyl,
  or
  —C≡C—;
$W_2$ is a monovalent radical selected from the group consisting of the following substituents:
$R^2$, which is alkyl or H;
Si-alkyl or Si-alkoxy;
alcohol;
ketone;
carboxyl;
amide; and
acyl; or
the substituents $T_1$, $T_2$, $T_3$ and $T_4$ form in pairs, when they are situated at two adjacent points in the formula (II), a saturated or unsaturated hydrocarbonaceous chain;
and with the condition that at least one substituent $T_1$ and/or $T_2$, which are identical or different, represent(s) a monovalent radical of following formula (V):

$$Z_1-Z_2 \quad (V)$$

in which:
$Z_1$ is a divalent hydrocarbonaceous radical, and
$Z_2$ is a monovalent radical selected from the group consisting of:
  a ($C_5$—$C_{30}$)cycloalkyl radical having at least one heteroatom in the ring, and
  a ($C_6$—$C_{30}$)aryl radical having at least one heteroatom in the aromatic ring,
$L_\alpha$ and $L_\beta$ are ligands which are identical to or different from each other and each represent:

$$Z^1\!=\!=\!=\!Z^2 \quad \text{or} \quad (III.1)$$

(III.2)

wherein, in these formulae (III.1) and (III.2):
$Z^1$, $Z^2$, $Z^3$, $Z^4$, $Z^5$ and $Z^6$ each independently represent:
  hydrogen,
  halogen, cyano, or a saturated or unsaturated, electron-withdrawing or non-electron-withdrawing, hydrocarbonaceous group, or two vicinal $Z^1$ to $Z^6$ groups together form an electron-withdrawing or non-electron-withdrawing ring which optionally comprises heteroatoms;

or $L_\alpha$ and $L_\beta$ together form the ligand $L_\delta$ of formula (IV):

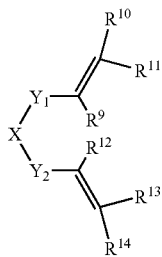

(IV)

in which:

$Y_1$ and $Y_2$ represent, independently of each other, $CR_aR_b$ or $SiR_cR_d$;

X represents O, $NR_e$ or $CR_fR_g$;

$R^{10}$, $R^{11}$, $R^{13}$ and $R^{14}$, which are identical or different, are selected from the group consisting of a hydrogen atom, an alkyl group and an aryl group optionally substituted by alkyl;

$R^9$, $R^{12}$, $R_a$, $R_b$ and $R_e$ are selected independently from the group consisting of a hydrogen atom; an alkyl group; an acyl group; an aryl group optionally substituted by alkyl; a cycloalkyl group optionally substituted by alkyl; and an arylalkyl group in which the aryl part is optionally substituted by alkyl;

$R_c$ and $R_d$ are selected independently from the group consisting of alkyl; aryl optionally substituted by alkyl; cycloalkyl optionally substituted by alkyl; and arylalkyl in which the aryl part is optionally substituted by alkyl; or when $Y_1$ and $Y_2$ independently represent $SiR_cR_d$, two $R_c$ groups bonded to two separate silicon atoms together form a chain of the formula:

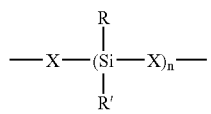

in which n is an integer from 1 to 3; X is as defined above; R and R', which are identical or different, have any one of the meanings given above for $R_e$, it being understood that, when n is 2 or 3, only one silicon atom of the said chain may be substituted by one or two alkenyl or alkynyl groups; or when $Y_1$ and $Y_2$ independently represent $SiR_cR_d$, two $R_c$ groups bonded to separate silicon atoms together form a saturated hydrocarbonaceous chain, the two $R_c$ groups forming, together with the said silicon atoms and X, a 6- to 10-membered ring; or when $Y_1$ and $Y_2$ independently represent $CR_aR_b$, two $R_a$ groups bonded to separate carbon atoms together form a saturated hydrocarbonaceous chain, the two $R_a$ groups forming, together with the carbon atoms which carry them and X, a 6- to 10-membered ring; and $R_f$ and $R_g$ represent, independently of each other, a hydrogen atom; an alkyl group; an acyl group; an aryl group optionally substituted by alkyl; a cycloalkyl group optionally substituted by alkyl; an arylalkyl group in which the aryl part is optionally substituted by alkyl; a halogen atom; an alkenyl group; an alkynyl group; or an $SiG_1G_2G_3$ group where $G_1$, $G_2$ and $G_3$ are, independently of one another, alkyl; alkoxy; aryl optionally substituted by alkyl or alkoxy; or arylalkyl in which the aryl part is optionally substituted by alkyl or alkoxy.

26. A metal complex or catalyst according to claim 25, wherein M is Pt, Pd or Ni in the zero oxidation state.

27. A metal complex according to claim 25, wherein $L_\alpha$ and $L_\beta$ together form a ligand $L_\delta$ of formula (IV) in which $Y_1$ and $Y_2$ either both represent $CR_aR_b$ or both represent $SiR_cR_d$, so that the complexes have the formula (IV.1) or the formula (IV.2):

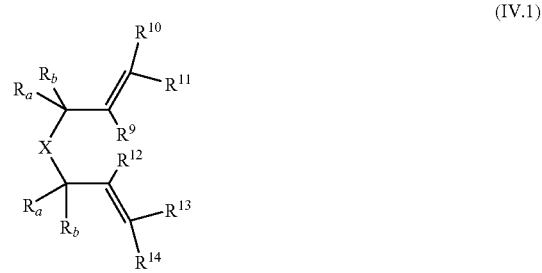

(IV.1)

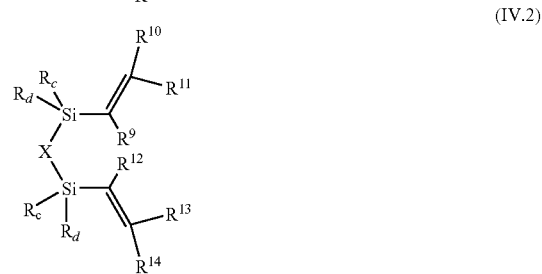

(IV.2)

wherein the two $R_a$ groups, the two $R_b$ groups, the two $R_c$ groups and the two $R_d$ groups are identical to one another and $R^9=R^{12}$; $R^{10}=R^{14}$; and $R^{11}=R^{13}$.

28. A metal complex or catalyst according to claim 25, having the formula (I.1):

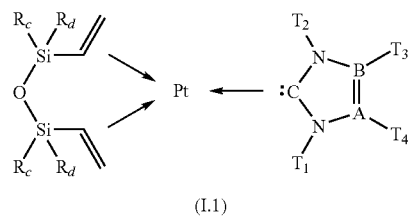

(I.1)

in which:

$T_1$ and $T_2$ are identical and are as defined in claim 25;

$T_3$ and $T_4$ are as defined in claim 25; and and $R_c$ and $R_d$ are as defined in claim 25.

29. A process for the hydrosilylation of olefins or of acetylenic derivatives, said process comprising heating a composition according to claim 1 at about 100° C. or greater to crosslink its -A- and —B— polyorganosiloxane components.

30. A process for the hydrosilylation of olefins or of acetylenic derivatives, said process comprising heating at least one PolyOrganoSiloxane -A- (POS) carrying ethylenic and/or acetylenic unsaturations and at least one polyorganohydrosiloxane —B—, in the presence of a metal complex or catalyst as defined in to claim 25 at about 100° C. or greater to crosslink said -A- and —B— components.

31. The process according to claim 29, wherein the catalyst C in the composition comprises at least one ligand $L_\alpha$ or $L_\beta$ of formula (III.1) or (III.2).

32. The process according to claim 29, wherein the composition comprises at least one inhibitor -D- which is a ligand $L_\alpha$ or $L_\beta$ of formula (III.1) or (III.2).

* * * * *

UNITED STATES PATENT AND TRADEMARK OFFICE
CERTIFICATE OF CORRECTION

PATENT NO. : 7,563,741 B2 Page 1 of 1
APPLICATION NO. : 10/515319
DATED : July 21, 2009
INVENTOR(S) : Oliver Brummer et al.

It is certified that error appears in the above-identified patent and that said Letters Patent is hereby corrected as shown below:

On the Title Page, Item [22] (PCT Filed): change "2003" to --2002--.

Signed and Sealed this

Twenty-second Day of September, 2009

David J. Kappos
*Director of the United States Patent and Trademark Office*